United States Patent [19]

Campbell et al.

[11] Patent Number: 6,047,259

[45] Date of Patent: Apr. 4, 2000

[54] INTERACTIVE METHOD AND SYSTEM FOR MANAGING PHYSICAL EXAMS, DIAGNOSIS AND TREATMENT PROTOCOLS IN A HEALTH CARE PRACTICE

[75] Inventors: Scott Douglas Campbell, Portland, Oreg.; Mark Howard, Vancouver, Wash.

[73] Assignee: Medical Management International, Inc., Portland, Oreg.

[21] Appl. No.: 09/001,379

[22] Filed: Dec. 30, 1997

[51] Int. Cl.[7] .......................... G06F 159/00; G06F 17/60
[52] U.S. Cl. ..................................... 705/3; 705/2
[58] Field of Search .............................. 705/2, 3

[56] References Cited

U.S. PATENT DOCUMENTS

| | | | |
|---|---|---|---|
| 5,065,315 | 11/1991 | Garcia | 705/2 |
| 5,072,383 | 12/1991 | Brimm et al. | 705/2 |
| 5,077,666 | 12/1991 | Brimm et al. | 705/2 |
| 5,517,405 | 5/1996 | McAndrew et al. | 706/45 |
| 5,583,758 | 12/1996 | McIlroy et al. | 705/2 |
| 5,713,350 | 2/1998 | Yakota et al. | 600/300 |
| 5,715,451 | 2/1998 | Marlin | 707/104 |
| 5,724,580 | 3/1998 | Levin et al. | 707/104 |
| 5,794,208 | 8/1998 | Goltra | 705/3 |
| 5,823,948 | 10/1998 | Ross, Jr. et al. | 600/300 |
| 5,834,253 | 12/1998 | Rensimer et al. | 705/2 |
| 5,842,175 | 11/1998 | Andros et al. | 705/3 |

OTHER PUBLICATIONS

Maroney, Martha, "Leapin' Lizards: Business Solution I,"*Microsoft Developer Network News*, May/Jun., 1995.
Brochure, "Client–Server Solutions—VETSMART," © Microsoft Corporation 1994.
Brochure, "Client–Server Solutions—VETSMART," © Microsoft Corporation 1995.

*Primary Examiner*—Gilberto Barrón, Jr.
*Assistant Examiner*—James W. Myhre
*Attorney, Agent, or Firm*—Klarquist Sparkman Campbell Leigh & Whinston, LLP

[57] ABSTRACT

A software system for managing a health care practice includes interactive software tools for conducting a physical exam, suggesting tentative diagnosis, and managing a treatment protocol. The physical exam software guides the user through a physical exam, prompting the user for input and dynamically generating context sensitive questions based on prior input. The diagnosis software generates a list of possible diagnoses based on the observations recorded from the physical exam. The user can interactively select a diagnosis by selecting a diagnosis from a rule out list and watching the display as the system dynamic updates the status of unresolved symptoms. The user can also select a treatment protocol, which is integrated with future physical exams. The treatment protocol is integrated such that future exam sessions reflect the status of the treatment protocol and remind the user which services need to be performed and when they should be performed.

22 Claims, 8 Drawing Sheets

FIG. 3

Examination Room Status — 300

Mary Louden　　Coal　　M　　Canine - Retriever Labrador
　Basic　　Age 6 months　　80.00 lbs — 302

Presented Complaint
Service Category: Preventative Care
Service Perscription: Vaccinations/Deworming — 304

306

Doctor: [　　　]　　Time In: 10:54:44 — 310
[　　　]　　Elapsed: 00:01
Video: [　　　　　]　　☐ Exam Room — 312

[ Ready For Check Out ]　　[ Exit ]

Physical Condition — 400

Susan Singleton　　Willie　　MN　　Canine - Shih Tzu — 402
　Age 6y/10m　　12.00 lbs

Presenting Complaint
Service Category: Preventative Care
Service Description: Vaccination/Deworming — 404
Further Description: Check Ears Preventative Care — 406
| | | |
|---|---|---|
| ☐ - due now | ☐ Canine Cough/Bordete* | ☐ Lyme Disease |
| ☐ - due soon | ☐ Corone Virus | ☐ Parvo Virus |
| ☐ - ordered | ☐ Distemper Combination | ☐ Rabies Virus |
| ☐ - don't give | ☐ Heartworm Antibody | ☐ Thyroid Test - reference |
| ☐ - current | ☐ Intestinal Parasite Fecal | ☐ |

Tentative Diagnosis History
None — 408

☐ Overall Condition
☐ Coat And Skin
☐ Ocular
☐ Otic
☐ Oral/Nasal
☐ Respiratory
☐ Cardiovascular
☐ Prodeminal
☐ Urogenital
☐ Perineal
☐ Musculoskeletal
☐ Neurological
☐ Behavioral — 410

[ Exam Check-Out ]　[ Suspend Exam ]　[ Exam Completed ]　☐ — 420

Overall Condition — 500

| James Benson | Tail Back | M | Feline - DLH |
|---|---|---|---|
| | Age 2y/5m | 8.00 lbs | |

Overall Condition (510)
- ◉ Excellent
- ○ Good
- ○ Needs Imprvment

Dehydration (512)
- No ▼

Temperature (514)
- 101.40 ▲▼
- ○ Subnormal
- ◉ Normal
- ○ Elevated

Temperature History (520)
| 10/17/96 | 101.40 |
| 03/26/96 | 101.40 |

Graph Temperature (522)

Recommended Care Declined (530)
- None

Environment (516)
- Leash Walked/Park ▼

The following questions are optional, but if answered, will help us develop better ways to help your pet and family and help us learn about the causes of pet behavioral problems and the advantages of human/pet bond.

| Hours Per Day w/Pet | # Of Human Children Under 16 | Where Was Pet Acquired |
|---|---|---|
| No Answer ▼ | No Answer ▼ | No Answer ▼ |

| # Of Rooms In Home | Boarding Practice When Away | Age Of Pet When Acquired |
|---|---|---|
| No Answer ▼ | No Answer ▼ | No Answer ▼ |

| # Of Pets You Have Owned | Reason For Pet | Character Of Relationship w/Pet |
|---|---|---|
| No Answer ▼ | No Answer ▼ | No Answer ▼ |

Related Video List: Nutrition ▼  — 550

✓ (540)  STOP (542)  △ (544)  (546)  🔔 (548)  📁 (504)

Abdominal Exam - Screen 2

| Valerie Yray | Blinte | M | Canine - Mastiff |
|---|---|---|---|
| | Age 3y/1m | 100 lbs. | |

Check abnormalities

Kidneys
| Left | Right | |
|---|---|---|
| ☐ | ☐ | Painful |
| ☐ | ☐ | Enlarged |
| ☐ | ☐ | Masses |
| ☐ | ☐ | Shrunken |
| ☐ | ☐ | Not Palpable |

Spleen
- ☐ Painful
- ☐ Enlarged
- ☐ Masses
- ☐ Not Palpable

Bladder
- ☐ Painful
- ☐ Distended
- ☐ Thickened Walls
- ☐ Masses
- ☐ Stones/Palpable
- ☐ Not Palpable

Prostate
- ☐ Painful
- ☐ Distended
- ☐ Not Palpable

Related Video List: The Complete Health Exam ▼

✓  STOP  △   🔔  📁

FIG. 9

Diagnosis — 902

Shandra Tillman    Princess    FS    Feline - DSH
Basic    Age: 6y/9m    10.00 lbs

| Abnormal Observations | Diagnosed Removed |
|---|---|
| Shaking Head or Scratching E | D |
| Trouble Hearing - Yes | |
| Bad Odor in Ears - Yes | D |
| Tartar on Teeth - Found | |

904
920

Remove Syptom From Diagnosis

Unresolved Symptoms   2
910

Exit    Healthy Pet
918    916

Rule Out List
Dental Pockets
Incisors Loose
Molars Loose    906
Premolars Loose
Tooth Exposed Roots

Tentative Diagnosis
| | |
|---|---|
| Otitis Externa | Needs protocol |
| Conjunctivitis | Undergoing Therapy |
| Dental Calculi | Client Postponed |

908

Search For A Diagnosis    Protocol
912    914

Diagnostic Protocol — 1002

Shandra Tillman    Mr. Mario Wh    MN    Feline - Siamese
Basic    Age 10 months    8.00 lbs Tentative Diagnosis: Otitis Media (med)

1004

Recommended Therapy
| | |
|---|---|
| Otoscopic Exam - complete | Required |
| Ear Swab & Microscopic Exam | Required |
| Immobilizing Agent Injection | Recommended |
| Ear Cleaning - brief | Required |
| Anti-Inflammatory Injections | Recommended |
| Anti-Inflammatory Oral Medicat | Recommended |
| Antibiotic Injections | Recommended |
| Antibiotic Oral Medications | Recommended |

1006

Diagnosis Status
○ Prescribe Therapy
◉ Under Therapy
○ Therapy Not Indicated
○ Further Defined
○ Resolved
○ Stable/Persistent/Chronic
○ Dr. Postpones Therapy
○ Client Postpones Therapy
○ Client Refuses Care

1008

Estimate — 1010
Additional Therapy
Continue — 1012

Estimate

Shandra Hillman

| Office Visit: Wellness Plan 1.x | | To Do | Princess |
|---|---|---|---|
| Opthalmic Exam – complete | | To Do | Princess |
| Opthalmic Exam – complete | | To Do | Princess |
| Oteoscopic Exam – complete | | To Do | Princess |
| Oteoscopic Exam – complete | | To Do | Princess |
| Oteoscopic Exam – complete | | To Do | Princess |
| Ear Cleanup – brief | 5.89 | To Do | Princess |
| Ear Cleanup – brief | 5.89 | To Do | Princess |
| Ear Cleanup – brief | 5.89 | To Do | Princess |
| Intestinal Parasite Fecal Exam | | To Do | Princess |
| Ear Swab & Microscopic Exam | 14.82 | To Do | Princess |
| Ear Swab & Microscopic Exam | 14.82 | To Do | Princess |
| Ear Swab & Microscopic Exam | 14.82 | To Do | Princess |

Therapy

Shandra Tillman   Princess   FS   Feline – DSH
Basic   Age: 6y/9m   10.00 lbs

View:
● All
○ To Do
○ Done

| Description | Rcv'd Dt | Qty | Status | Dosage & Freq |
|---|---|---|---|---|
| Intestinal Parasite Fecal | / / | 1 | To Do | |
| Office Visit: Wellness P1 | / / | 1 | To Do | |
| Physical Exam: Wellness P | / / | 1 | To Do | |

Make All Done
Print Labels
Remove Items

Tentative Diagnoses
| 11/23/96 Conjunctivitis | Needs protocol |
| 05/29/96 Dental Calculi | Client Postponed |

Physical Exam   Continue

INTERACTIVE METHOD AND SYSTEM FOR MANAGING PHYSICAL EXAMS, DIAGNOSIS AND TREATMENT PROTOCOLS IN A HEALTH CARE PRACTICE

FIELD OF THE INVENTION

The invention relates to an automated health care management system and more specifically relates to a graphical and interactive medical office management system for automatically generating client education information, conducting a physical examination, diagnosing medical conditions, and managing a therapy protocol.

BACKGROUND OF THE INVENTION

With rising health care costs, it is imperative that health care providers provide health services efficiently and cost effectively. At the same time, the administrative demands of medical record keeping, billing and managing a medical practice have become more burdensome. In particular, health care providers must be thorough and keep detailed records of medical exams to accurately document observations and services that have been provided. A number of software tools are available to help assist physicians in conducting medical diagnoses and medical record keeping. However, these tools have a number of deficiencies.

Some software programs used to diagnose medical problems start with the physician making a tentative diagnosis, and then proceed to collect medical observations which support, or clarify the tentative diagnosis. This can lead to inaccurate conclusions since the medical exam is likely to be biased by the original diagnosis.

Another limitation of many software systems used in medical practices is that they do not effectively manage the workflow within the hospital. In addition to diagnosing medical problems, it is useful to have a system for tracking the flow of patients in a hospital or medical office. Present systems do not effectively integrate workflow tracking with medical diagnosis functions.

Another limitation of existing software systems for medical practices is that they do not integrate treatment or therapy within the medical exam process. This is a significant drawback in medical diagnosis software because it does not provide the client or patient with information that will help them understand the cause of an ailment or educate them so that they can make educated decisions on treatment of it.

SUMMARY OF THE INVENTION

The invention provides a computer-implemented method and system for tracking workflow through a medical facility (e.g., hospital, clinic, office, etc.), managing medical exams of patients in the facility, and managing a treatment protocols for the patients. The medical exam portion of the system is used to guide a health care provider through an exam, generating context-sensitive questions and possible diagnoses. One implementation of the invention is specifically adapted for a veterinary practice, where the client is the pet owner and the patient is the client's pet. However, the features of the invention can also be used in human medical practices.

When installed in a medical office or hospital, the system software of the invention can be executed in a network configuration or in a stand-alone computer. The system software displays interactive user interface screens for conducting an interactive medical exam, generating diagnoses of abnormal observations, and managing a treatment protocol. The treatment protocol can be integrated with the interactive medical exam component of the system. For example, the doctor can select a treatment protocol from a user interface displaying computer generated diagnoses. In response, the system schedules the treatment protocol such that future interactive exam sessions display reminders to perform services in the protocol, and prompt the user to make observations related to the selected diagnoses. Once the physical exam is complete, and has been signed off by the doctor, the examination results are read-only. Additional, or subsequent medical observations may be added to the medical record through the use of medical notes. Medical notes may either be pre-formatted, or free-hand.

The interactive medical exam component of the system displays physical exam screens that guide the user through a complete medical exam. The screens display predetermined observations and enable the user to select among the observations to record abnormal findings. The system dynamically updates the patient's record and evaluates the input to generate additional context sensitive prompts to record additional observations.

At the end of an exam, the system evaluates the abnormal observations and generates a list of possible diagnoses. The system displays an interactive diagnosis screen including a list of the diagnoses. The user can then select from the list generated by the system (the rule out list) to select tentative diagnosis. As the user does so, the system updates a list of abnormal findings to show whether they are resolved by the selected diagnosis. The user can then prescribe a treatment protocol by selecting a tentative diagnosis.

The system includes a scheduler that automatically updates the patient's records to reflect that the patient is under treatment. In subsequent interactive physical exam sessions managed on the system, the physical exam screens display status information about the treatment protocol. This feature helps to ensure that the treatment protocol will be followed in subsequent physical exam sessions.

Additional features and advantages of the invention will become more apparent from the following detailed description and accompanying drawings.

BRIEF DESCRIPTION OF THE DRAWINGS

FIG. 3 is an example of a status screen used to check the status of a patient in the hospital.

FIG. 4 is an example of a physical exam overview display generated by an implementation of the invention.

FIG. 5 illustrates an example of an interactive physical exam display used to record information about a patient's overall condition.

FIG. 6 illustrates an example of a supplemental user interface screen that is triggered in response to an abnormal observation to prompt the user for additional input related to the abnormal observation.

FIG. 9 illustrates an example of an interactive user interface screen used to display diagnosis generated by the system and to guide the user in selecting a tentative diagnosis.

FIG. 10 is an example of the diagnostic protocol screen used to manage a treatment protocol.

FIG. 11 is an example of an interactive user interface screen used to display an estimate of the cost of services to be provided or already provided to a patient.

FIG. 12 is an example of an interactive user interface screen used to manage the administration of a service item under a treatment protocol.

DETAILED DESCRIPTION

Introduction

The invention is directed toward a method and system for managing a medical care practice. The specific implementation described below is a system for managing a veterinary practice, including software tools for interactively guiding a user through a medical examination, providing tentative diagnosis for abnormal observations recorded during the exam, selecting a diagnosis and treatment protocol, and integrating the treatment protocol into future interactive exam sessions.

System Architecture

One implementation of the system is developed for a network computing environment in a veterinary hospital. This system comprises a series of program modules running in a Windows® NT operating system environment. The program modules are implemented in the FoxPro® database programming environment. In a typical configuration, the program modules of the system are organized in a client server architecture. Several computers throughout the hospital are equipped with client software, which can access server software on a server via the network. The client software typically provides a graphical user interface comprising a number of screens in a windowing environment for prompting the user for input and displaying output.

In one particular client server implementation, the server executes database management software and maintains a series of relational databases (tables). The client and server software is developed using the FoxPro® database development tools. The client-server software is written in FoxPro® database for Windows® NT operating system, and uses the native FoxPro® database file structures.

The server software coordinates communication among the client computers, manages a database of client and patient data, monitors data supplied via the client computers, performs data processing functions on the data as observations are made, and dynamically updates the display data displayed on the client computer. While the preferred implementation for a hospital setting is a network environment, many of the software functions, including the user interface and data management functions can be performed on a single computer.

Figure 1:
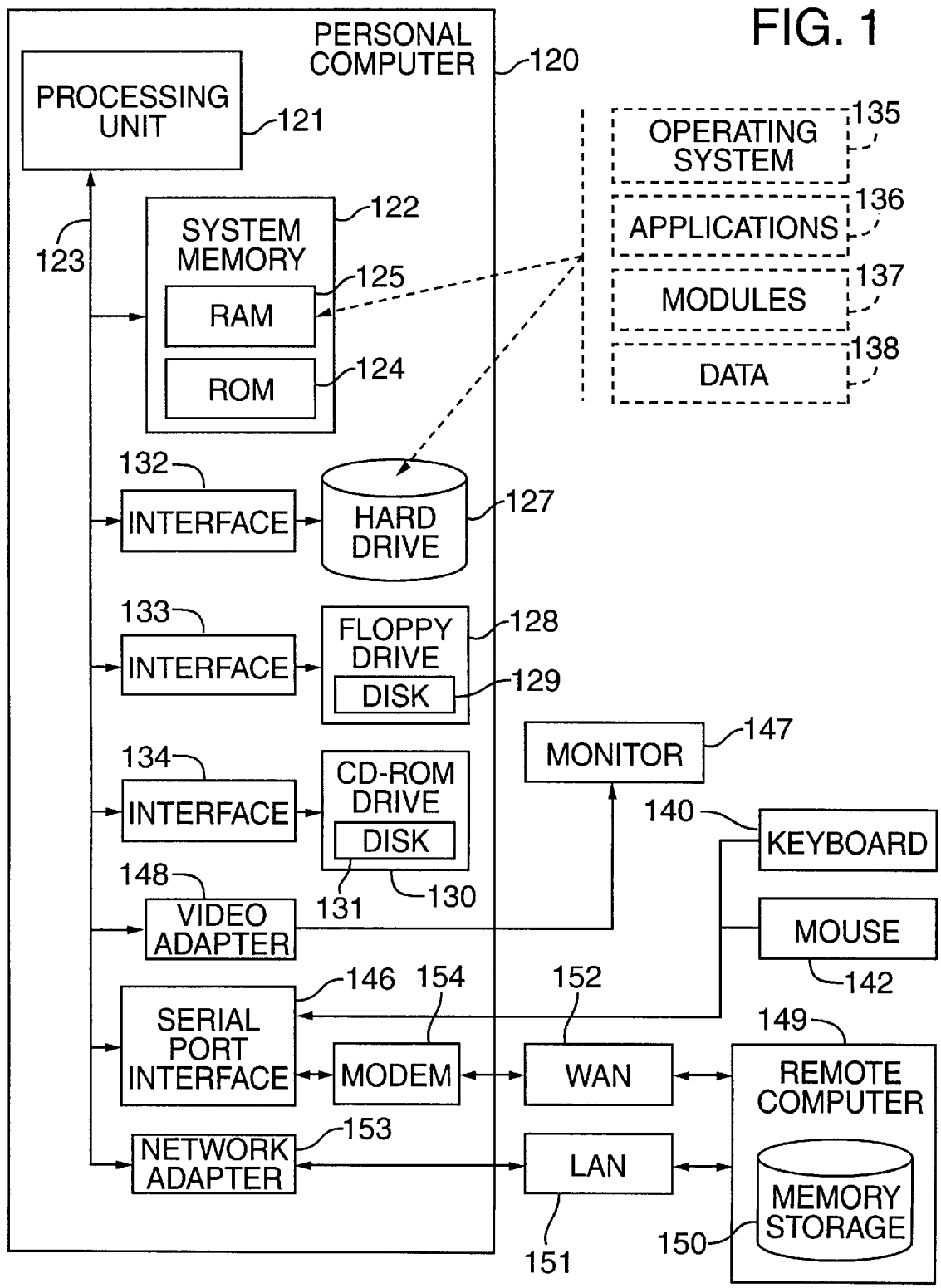
FIG. 1 is a block diagram of a computer that serves as an operating environment for medical office management software.

FIG. 1 and the following discussion are intended to provide a brief, general description of a suitable computing environment for the server and client computers. As noted above, the system software is implemented in a series of program modules, comprising computer executable instructions executed either on a server or client computer. Generally, program modules include routines, programs, components, data structures, etc. that perform particular tasks or implement particular abstract data types. The medical system software of the invention may be ported to other computer system configurations, including hand-held devices, multiprocessor systems, microprocessor-based or programmable consumer electronics, minicomputers, mainframe computers, and the like.

The invention is typically practiced in distributed computing environments where tasks are performed by remote processing devices that are linked through a communications network. In a distributed computing environment, program modules may be located in both local memory of a client computer and remote memory such as in the server computer.

FIG. 1 illustrates an example of a computer system that serves as an operating environment for the invention. The computer system includes a personal computer 120, including a processing unit 121, a system memory 122, and a system bus 123 that interconnects various system components including the system memory to the processing unit 121. The system bus may comprise any of several types of bus structures including a memory bus or memory controller, a peripheral bus, and a local bus using a bus architecture such as PCI, VESA, Microchannel (MCA), ISA and EISA, to name a few. The system memory includes read only memory (ROM) 124 and random access memory (RAM) 125. A basic input/output system (BIOS), containing the basic routines that help to transfer information between elements within the personal computer 120, such as during start-up, is stored in ROM 124. The personal computer 120 further includes a hard disk drive 127, a magnetic disk drive (floppy drive, 128), e.g., to read from or write to a removable disk 129, and an optical disk drive (CD-ROM Drive, 130), e.g., for reading a CD-ROM disk 131 or to read from or write to other optical media. The hard disk drive 127, magnetic disk drive 128, and optical disk drive 130 are connected to the system bus 123 by a hard disk drive interface 132, a magnetic disk drive interface 133, and an optical drive interface 134, respectively. The drives and their associated computer-readable media provide nonvolatile storage of data, data structures, computer-executable instructions (program code such as dynamic link libraries, and executable files), etc. for the personal computer 120. Although the description of computer-readable media above refers to a hard disk, a removable magnetic disk and a CD, it can also include other types of media that are readable by a computer, such as magnetic cassettes, flash memory cards, digital video disks, Bernoulli cartridges, and the like.

A number of program modules may be stored in the drives and RAM 125, including an operating system 135, one or more application programs 136, other program modules 137, and program data 138. A user may enter commands and information into the personal computer 120 through a keyboard 140 and pointing device, such as a mouse 142. Other input devices (not shown) may include a microphone, joystick, game pad, satellite dish, scanner, or the like. These and other input devices are often connected to the processing unit 121 through a serial port interface 146 that is coupled to the system bus, but may be connected by other interfaces, such as a parallel port, game port or a universal serial bus (USB). A monitor 147 or other type of display device is also connected to the system bus 123 via an interface, such as a video adapter 148. In addition to the monitor, personal computers typically include other peripheral output devices (not shown), such as speakers and printers.

The software system of the invention is typically implemented in a network configuration in a veterinary hospital, though it can be implemented on a single PC. In network installations, there are several personal computers like the one depicted in FIG. 1. Each of the personal computers (such as PC 120) operate in a networked environment using logical connections to one or more remote computers, such as a remote computer 149. The remote computer 149 is usually a server, but can also be a router, a peer device or other common network node. The remote computer includes many or all of the elements described relative to the personal computer 120, although only a memory storage device 150 has been illustrated in FIG. 1. The logical connections depicted in FIG. 1 include a local area network (LAN) 151 and a wide area network (WAN) 152. Such networking environments are commonplace in offices, enterprise-wide computer networks, intranets and the Internet.

When used in a LAN networking environment, the personal computer 120 is connected to the local network 151 through a network interface or adapter 153. When used in a WAN networking environment, the personal computer 120 typically includes a modem 154 or other means for establishing communications over the wide area network 152, such as the Internet. The modem 154, which may be internal or external, is connected to the system bus 123 via the serial port interface 146. In a networked environment, program modules depicted relative to the personal computer 120, or portions of them, may be stored in the remote memory storage device. The network connections shown are examples only and other means of establishing a communications link between the computers may be used.

Figure 2:
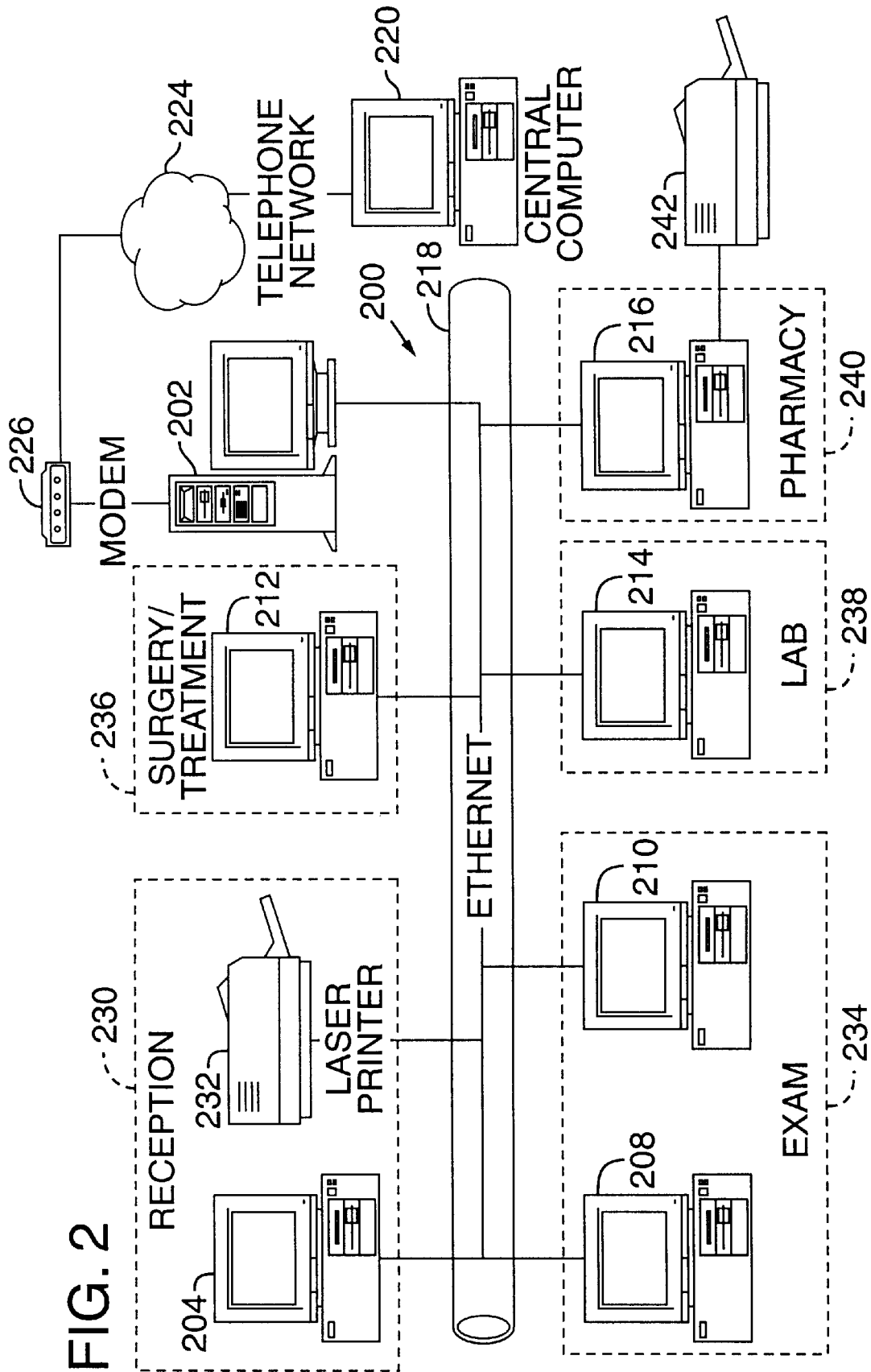
FIG. 2 is a block diagram illustrating a computer network for managing client and patient medical data in a veterinary hospital.

FIG. 2 is a block diagram illustrating a typical network configuration 200 used to implement system software of the invention in a veterinary hospital. The network configuration 200 includes a server computer 202 and a number of personal computers 204–214 connected together on a computer network 218. In this configuration, the network is an ethernet network, but any other conventional computer network can be used to implement the system. The computers are distributed throughout the hospital and are designed to provide access to some common functions as well as some special purpose functions unique to the particular computer. Some of the client computers have special attributes that enable them to perform functions relevant to the part of the hospital where they are located: 1) the reception computer 204 checks clients and patients in and out of the office and handles billing functions; 2) the exam room computers 208–210 are used by doctors and nurses to conduct medical examinations, to make diagnoses, and select a treatment protocol; 3) surgery/treatment computers 212 are located at surgery and treatment areas in the hospital and provide patient status data (e.g., traffic control, patient triage information such as names of patients, status, presenting complaint, to-do lists) as well as similar functions as the exam room computers 208–210; 4) the lab computer 214 interfaces with lab equipment and is used to enter information from lab tests; and 5) the pharmacy computer 216 is used to fill prescriptions, conduct inventory control on pharmaceuticals and medical supplies, order supplies, and provide database search functions.

While each computer is designed to perform certain types of functions in the office, many of the computers have common features and provide access to the same client and patient information and server functions. For example, if authorized, a doctor can look up client information on any of the computers in the network.

Communication Among Client Nodes

Each of the computers can transfer messages to each other via a queue on the server. When the client software running on a computer in the network wishes to communicate with other client software, the client sends a message to the server. The message can indicate that some event has taken place or it can request an action. The server places this message in a shared queue in main memory on the server.

Each of the client computers and the server periodically scan the queue for messages. In this implementation, the queue is a database file, and the clients scan the queue by performing a database query on the file. If a client finds that one of the messages is intended for it, it performs the requested action sought in the message. When the requested action is processed, the server deletes the record requesting the action. By updating the queue in this manner, each of the clients on the network are informed that the event or requested action in the message has been processed.

Authenticating Access to Server Functions and Data

The server's database management software manages access to server functions and data in the databases by authenticating access to databases or functions on the data. Specifically, the server 202 maintains a table that lists computers and users indexed to data and functions that the computer or user can access. Another authentication table tracks provider teams, which are typically comprised of a doctor, nurse and receptionist. This table keeps track of who is logged into the system and determines, based on who is logged in, what functions and data each person will be able to access. For example, if a nurse is checked in, the nurse will be able to make preliminary medical observations, but will not be able to access diagnostic screens and make diagnosis.

The server controls access to server functions and data via a table indicating the name of each client computer connected to the network and a list of functions that each client is able to access. In this particular implementation, the server uses the Windows® operating system computer name to identify each computer. The server maintains a table of all computers which are attached to the system. This table includes the specific functions which the client computer is intended to perform. This enables the server to control which functions each client is able to access.

The client server model enables the provider teams to work together on a common set of data. As a member of a team completes part of an exam or conducts some treatment using the system, the server software dynamically updates the data so that it will be properly reflected to other users when they access it. For example, if a lab technician enters the test results of a blood test on the lab computer, a doctor in the exam room will be able to get this information via the exam room computer.

In the current implementation of the system, the client computers each present a graphical user interface in a windowing environment. The user interface displays text and graphical information about clients and patients (the client's pets) in Windows® operating system. The users of the system enter input using a variety of input devices including a key board and pointing devices such as a mouse, trackball, touch screen membrane or touch pad.

The Link to a Remote Computer

The computer network shown in FIG. 2 is an example of the network configuration in a typical hospital. A number of these network configurations around the country are connected to a central computer 220. As shown in FIG. 2, the server computer 202 is connected to a remote computer 220, which acts as the central computer for several hospitals. The central computer periodically dials-up the server via the telephone network 224 and obtains a copy of the hospital's data. All information at the hospitals which has changed is gathered into the central system.

The server, in this example configuration shown in FIG. 2, is connected to the phone network via a modem 226. The central computer 220 also controls administrative and billing functions. One important function of the central computer is how it administrates wellness plans. Specifically, the central computer is responsible for handling billing of clients that have selected wellness plans.

The Reception Computer

As introduced above, the functions of each of the client computers are generally related to where they are located in the hospital. In the receptionist area 230 of the hospital, the receptionist computer 204 is designed primarily to check patients in and out of the hospital and monitor client and patient traffic by keeping track of who is in the hospital, where they are, and how long they have been in the hospital. Typically there are at least two reception computers. Each them share a printer 232 used to print invoices and client education information.

The Exam Room Computers

In the exam rooms 234 of the hospital, the exam room computers 208–210 are used to conduct medical exams. The physical exam software modules walk the nurse and doctor through an entire medical exam. The software displays exam screens that prompt the user for input. The user interface screens guide the user by displaying a list of items that require observation. For some items, the software will not allow the user to proceed without entering an observation. At the end of the physical exam, the physical exam software requires the doctor to sign off on the physical exam. The doctor can then proceed to invoke the diagnosis software.

The diagnosis software uses the observations made during the medical exam to prepare a rule out list and prescribe a treatment protocol. Diagnosis software running on the server uses the observations to generate a list of abnormal observations and tentative diagnosis. The doctor can then select a tentative diagnosis by positioning the cursor over a diagnosis and selecting it. By selecting a tentative diagnosis, the user triggers the generation of a treatment protocol. This treatment protocol can then be integrated into future medical exam sessions. It is integrated because procedures that need to be performed and observations that need to be made are identified in the graphical exam screens in follow-up visits. Thus, once a treatment protocol is selected, the system manages the administration of that protocol in future exam sessions.

The Surgery and Treatment Computers

In the example shown in FIG. 2, the surgery and treatment computers 212 are combined and are depicted as being in a single location 236 (e.g., a surgery and treatment area in the hospital). As emphasized above, it is not necessary to have separate computers for performing separate functions such as having a surgery computer for displaying triage information or a treatment computer for recording treatments on a patient as they are performed. Instead, surgery and treatment functions can be accessed from a single computer.

The Lab Computer

In the lab 238 of the hospital, the lab computer is used to check lab tests that have been ordered and to enter lab results. The lab functions of the system include an interactive user interface that enables members of a provider team to look up a patient and either enter lab results or view a list of tests that need to be performed for a patient. The user interface includes a laboratory screen, listing records including client name, patient name, name of a test, and when the test was ordered. The user can click on a record to select it and then proceed to a lab results screen by clicking on a button in the lab screen. The system will display a lab results screen, which prompts the user to type in the results and record the changes. When the user clicks on a button to record the changes, the changes get updated in a table used to store laboratory results and symptoms maintained for the patient.

The service items ordered for a patient, such as lab tests, are recorded in an accounting line item table. When a user enters a change in status for a lab test, the system updates the status of the service item corresponding to this test in the accounting line item table. In addition to updating the status in the accounting line item table, the system posts a note in the medical lab notes for the patient indicating that the test is complete.

The Pharmacy Computer

In the pharmacy 240 of the hospital, the pharmacy computer 216 manages the pharmaceutical products and processes requests for prescriptions. The pharmacy computer executes client pharmacy software that is integrated with the exam software in that it responds to requests to generate labels when a doctor enters a prescription in a prescription screen during the medical exam. The pharmacy computer 216 is connected to a printer 242 used to print prescription labels.

Having described the system architecture of a network configuration in a veterinary hospital, we now describe the software for managing a medical practice in more detail.

Tracking the Provider Team

The software system tracks user input to the system based on a provider team. As described above, users get access to the system and its functions based on their login name. Once logged in, a user has access to data and functions in the system. As observations are entered, these observations are attributed to the person that made them based on the login of the session. A session refers to the time period in which a user is logged in to the system and is accessing server functionality. As a member of the medical team takes an action and records this action through the user interface client, the system attributes the action to the person and team that took the action.

Tracking the provider team has implications on generating billing reports and productivity reports. In the system, activities of team members can be classified as a selling or providing. As products or services are provided to a client/patient, a member of the team enters the information on the user interface, typically by selecting the item on the user interface. These items are added to a file representing the client's bill and in addition are attributed to the provider team. Chargeable service or products provided by the team are attributed to a selling and providing person in a predetermined proportion, such as 55/45 percent. This enables the system to generate productivity reports for a provider based on individual product and service items. This feature also enables the system to give credit to the providers that are responsible for getting clients to sign up on a wellness plan, which is also administered on the server.

Tracking Patient Workflow

In addition to guiding a user through the physical exam and diagnosis process, the system also tracks the work flow in a medical facility such as a hospital or doctor's office. When a patient arrives, the patient is "checked into" the system. Throughout the visit, the system tracks the patient's progress through various stages of the visit, such as waiting in the lobby, undergoing a physical examination in an exam room, awaiting check-out, undergoing tests in the lab, hospitalized, etc. These stages generally correspond to different parts of the medical facility such as the lobby, exam room, lab, surgery room etc. However, it is important to emphasize that the stages do not have to be associated with separate physical locations, especially in a smaller facility where a single room is used for the medical exam, lab tests and surgery.

As the patient progresses through a visit, the system software guides the provider team through the visit by prompting the user for input needed to complete each stage. This input can include patient data, medical findings (or at least confirmation that examination is complete), or authorization from a doctor. When a member of the provider team completes a stage in the visit, such as checking in a patient or conducting a medical exam, the system tracks the flow by updating the status of the patient's visit in memory. In a client server configuration, this status information is maintained on the server so that members of the provider team can check the patient's status from different client computers. By tracking patient status in this manner, the system ensures that the patient's visit proceeds in an orderly manner, that all necessary services are provided, and that a complete record of an entire visit is recorded in the system. In addition, it gives the provider team an opportunity to track which patients are in the facility, what their current status is, and how long each patient has been in the facility.

Patient Check In

When a client brings a patient to the veterinary hospital, the first step on the system is to check-in the client and patient at the receptionist computer. The receptionist computer acts as an interface to the systems Appointment Scheduler and also provides a Reception screen that enables the user to change the status or location of patients within the hospital, as tracked by the server. The receptionist performs several tasks using the reception screen as a method of identifying the patient to service. These functions include checking patients into the hospital, assigning exam rooms, making appointments, making follow-up telephone calls, and performing patient check-out and cash receipts functions.

The reception screen is used to check in a client and the patient (the client's pet). If either the client or patient is new, the system presents screens to prompt the user for missing information. For patients, the system prompts the user for patient information such as: gender (male, female, unknown), whether neutered or spayed, noting of allergic reaction, tendency of a pet to bite, and whether pet is on wellness plan.

As part of the client check in procedure, the system may request the client to verify client information. At a client check in screen, the system will check whether the client has been in the hospital in the last 15 days. If so, the system will assume that the client information displayed in this screen is current. If not, the client screen will prompt the user to verify client information. The receptionist must enter input acknowledging that the client has signed a release to provide care to the patient. The entry of the release to the system is a critical event that must occur before the system will proceed to a medical exam. The receptionist can also enter a list of items that the client left with the pet. This information is useful at a check out screen, where the reception computer retrieves a list of these items from the server and displays them as reminder to return them to the client.

As part of the patient check in procedure, a receptionist enters the presenting complaint via the user interface of the reception computer. The reception computer sends the text describing the presenting complaint to the server, which in turn records it in the patient's medical record. A new medical record, with presenting complaint, is created for each visit of the patient to the hospital. Client computers load and display the presenting complaint (as well as other patient data) in a banner displayed in a variety of screens in client computers in the hospital when accessed by members of the provider team. The receptionist also enters the patient's weight and records the weight in the system. The entry of the weight information is another critical event that needs to occur before any exam or procedure can occur on the patient during the visit. For example, the system will not allow a user to execute the physical exam software for this patient without having this information recorded first.

When a user enters a request at a client computer to load physical exam software for a patient, the client computer sends the request to the server. The server checks the patient's data file to check whether a critical event (entry of the weight) has occurred. If not, the server will transfer a message to the client computer indicating the error and the reason for the error. The client computer will then display a message box to the user indicating that the critical event must occur before the physical exam can proceed.

A main control screen, accessible from the receptionist computer, tracks the status of patients relative to the traffic at the hospital. The server classifies patients as 1) Awaiting Pick Up, 2) Checking Out, 3) Missed Appointments, 4) In the Lobby, and 5) Scheduled to come in. Category 4 is broken into two further categories, using attributes assigned to the record in a traffic database: A) Scheduled to Come In, Drop Off; and Scheduled to come In, In Lobby.

This feature is implemented by dynamically tracking the patients in a hospital in a file on the server. The server maintains patient status table storing a dynamic list of all patients which are in the hospital at a given time. This table also includes the date and time the patient arrived, and the current physical location of the patient within the hospital. The server updates the table in response to messages from the clients that change the status of the patient. For example, when the reception computer checks in a patient, it also sends a message to the server indicating the name and status of the patient. The server places a time stamped record in the patient status table. As the patient proceeds through the hospital from reception, exam room, to check out, the client computers update the status of the patient by sending a message to the server indicating the patient and the current patient status.

Automatic Selection and Playback of Client Education Video

The system is programmed to playback client education videos for clients in the waiting room of the hospital. There are two ways to select a video in the system. One way is for the receptionist to select a video from a list. In this case, the receptionist specifies the video, the exam room, and a programmable delay period. In response, the server issues a command to the exam computer to queue the video and play it after the programmed delay period. The video is preferably stored on the client computer (e.g., the exam room computer) where it will be played back. The video will begin to play on the exam room computer after the delay period chosen by the receptionist elapses.

The second way to playback a video in the system is by automatic selection by the server. The server matches the patient in the hospital with a room where the patient is located using two tables: 1) the patient status table, which shows the patients currently in the hospital and each of the patients' current status; and 2) a client computer table, which maintains the status and identification of each computer in the hospital. When the patient is assigned to an exam room, the system matches the patient to the computer associated with that exam room. The server then evaluates a variety of attributes about the patient to select an appropriate video. One attribute is a patient record indicating the purpose of the visit. Other attributes used to select a video are the type of pet, the age of the pet, and the time of year. The server first tries to find a matching video for the purpose of the visit by text searching the list of videos for a topic that matches the purpose of the visit. Finding no matches, the server continues searching for matches based on other criteria in a predetermined order.

Physical Examination

Transferring from One "Room" to Another

Before the physical exam can begin, the receptionist has to check the patient into an exam room. The receptionist does this by entering the exam room number at the reception computer. The reception computer sends a message to the server, which in turn, updates the patient status table to reflect the location of the patient, e.g., the patient is in a medical exam in exam room 1.

Personnel in the hospital can check on the status of patients occupied in the exam room. FIG. 3 illustrates a screen diagram indicating a window for checking the status of an exam room. To bring-up this screen, a user can double click on the patient's name in the reception screen displayed by a client computer. As shown in FIG. 3, the Exam Room Status screen 300 is a graphical window divided into two primary sections: a banner 302 showing patient information; and a window 304 showing exam room status information. The banner 302 includes the client name, patient name, gender, weight, and species. The banner is also color coded so that the provider team can readily identify key information about the patient or client. Gender is depicted with colors (e.g., blue for male, and pink for female). A client with an overdue bill is depicted with a red colored banner (a client in "collection").

The window 304 includes a box 306 called "Presenting Complaint" that lists the service category, service description, and any further description. The window 304 also includes dynamically updated information such as the time of check-in 310 and elapsed time in the office 312.

This window also illustrates an example of how the system navigates a patient and client through an office visit. A user can change the status of a patient in the exam room by clicking on a control button 320 in the window. For example, in this screen, the user can indicate that the patient is ready for check out. This sends a message to the server, which updates the status of the patient. The reception screen can then be used to check out the patient.

The Physical Examination

When the nurse logs onto the computer located within the exam room, the physical examination for the patient assigned to the exam room is presented. No action is required on the part of the nurse to select the exam, the exam room, or the patient. The client computer in the exam room displays the Physical Examination Screen, populated with information about the patient that is checked into the exam room.

FIG. 4 shows an example of the Physical Examination Screen 400. This screen includes the following graphical elements: the client patient banner 402, the presenting complaint box 404, a preventative care box 406, a tentative diagnosis box 408, a series of buttons 410 that list and navigate to screens used to obtain input and guide the user through the physical exam, and control buttons 412–416 for changing the status of the exam.

The banner 402 and the presenting complaint box are the same features as shown in FIG. 3.

The preventative care box 406 lists preventative care services and their status in a color coded fashion. When a client signs up for a wellness plan for his or her pet, the system loads additional software components that are used to administer the plan. This is an example of such a feature. In this case, the physical exam screens display additional information about the status of the preventative care services provided under the plan. The physical exam screen prompt the user about the status of a preventative care service and tell the user when the service should be provided.

In this version of the software, the preventative care status is displayed in a color coded fashion. The possible status includes: Red=due now, Yellow=due soon, Blue=ordered this visit, White=don't give, and Green=current. This status information is dynamically updated on the server as a member of a provider team enters input indicating that a service has been performed. In addition, the system has a scheduler that determines when changes in status occur based on the order date and the current date. When the physical examination process is initiated, the server looks up the status of each preventive care item so that the most recent information can be returned to the client for display. This status information is maintained in an accounting sales line item table on the server.

The tentative diagnosis box provides the diagnosis history of the patient. This box lists diagnosis that have been made as result of previous physical exams. The diagnosis software is explained in further detail below. However, to summarize briefly, the server generates tentative diagnosis based on observations collected during the physical exam. When the doctor selects a diagnosis using the diagnosis tools, the server adds these to a diagnosis table. The server generates the diagnosis history from this table. From this window, the provider can retrieve more detailed medical history data, including diagnoses.

The physical exam buttons represent the top level in a hierarchy of physical exam screens. The physical exam is broken into the following areas:

1) Overall Condition
2) Coat and Skin
3) Ocular
4) Otic
5) Oral/Nasal

6) Respiratory
7) Cardiovascular
8) Abdominal
9) Urogenital
10) Perineal
11) Musculoskeletal
11) Neurological
12) Behavioral When the user clicks on any of these buttons, the system launches a new screen for the selected part of the physical exam. The interactive exam screens guide the user through the physical exam. As user enters information (by clicking on buttons or entering text), the server dynamically updates the database and evaluates the data to determine whether to prompt the user for additional information by displaying questions and supplemental screens that prompt the user to input medical observations.

During an initial exam, many of the observations listed in the exam screens default to normal. If an abnormal observation is checked, subsequent exams will default to the previous findings by displaying the abnormal observation as marked in a previous exam. In some instances where critical information is necessary, the user will not be allowed to exit from a screen until certain observations are made, as reflected by the user entering some observation.

Some observations trigger actions that need to be performed right away, and others trigger actions that can be performed later. In either case, the client monitors for this type of input, and when it detects the observation, it evaluates preprogrammed expressions to determine which actions should be performed right away or performed later. For actions that should be performed right away, it displays additional queries using message boxes or additional screens. As observations are made during the physical exam, the need to present additional screens is maintained in memory variables which control the operation and behavior of the exam as a whole, and the operation and behavior of individual sub-exam screens.

The user can proceed through the physical exam portions in any order, but must complete all parts of the exam before any diagnosis is performed. To reflect parts of the exam that are complete, the physical exam screen shown in FIG. 4 includes a status box (e.g., 420) next to each navigational button that links to the portions of the physical exam. These boxes are color coded to indicate the status of the corresponding part of the exam. In this version, green means all findings are normal in this part of the exam, red means that the nurse has marked abnormal findings for the doctor's review, and blue means that text questions were not answered by the doctor.

The control buttons across the bottom enable the user to control the status of the exam. For example, the user can choose to check out of the exam, to suspend the exam, or indicate that the exam is complete.

Example Exam Screens

FIG. 5 illustrates an example of a physical exam screen used to record information about a patient's overall condition. The Overall Condition Screen 500 includes the banner 502, a control bar 504 across the bottom, and a variety of graphical user interface controls for collecting input (text or cursor control device) and for displaying output (including numerical data, observations recorded as text, and graphical data generated by the server).

The graphical user interface controls prompt the user to enter information because they display an item to be observed and then give the user an option to make some observation for that item. For example, in this screen, the user can select the overall condition or temperature observation by checking a check button (e.g., 510, 512). The user can enter numerical data such as temperature via a graphical box 514 that allows the user to scroll through a range of numbers. In addition, the user can enter or select text input from drop-down boxes (e.g., 516).

The screens display patient data dynamically as well. For example the temperature history box 520 displays temperature observations. The user can also choose to display a graph of the temperature by clicking on the "graph temperature" button 522.

The system also documents when services have been offered and declined by the client. For example, the screen in FIG. 5 has a box 530 entitled "Recommended Care Declined" which lists any services that the client has declined in the past.

The data displayed in this and other exam screens is dynamic in that it is updated by the server soon after it is entered. Thus, the screens reflect up-to-the-minute data, some of which may have been entered just moments ago on the same or a different client computer. The interface screens are formatted to display information about a patient, and the system draws this information from the patient's records, which are updated each time new information is entered at any client computer. When the user selects a screen for display, the patient data in the display is drawn from the current patient records on the server.

When the user initiates the exam, the server evaluates the observations and determines which questions and warnings should be displayed to the user. As the user accesses screens in the exam, these warnings or questions form part of the display screen. Thus, the display changes based on prior recorded observations.

The Control Bar

Several of the physical exam screens have a control bar such as the one shown in FIG. 5. This control bar includes graphical control buttons that provide helpful functions during the exam. The example shown in FIG. 5 includes a check mark 540, a stop button 542, an exclamation point 544, a drop down list of videos 546, a warning bell 548, and a medical note pad editor 550.

The check mark is a navigational control that enables the user to tell the server that the user is ready to move on to the next screen. The stop button halts the exam and returns the client to the physical exam screen. The exclamation point enables a nurse to check a part of the exam to call it to the doctors attention. This input event tells the doctor that he or she needs to check this part of the exam. The screen is marked in blue to tell the doctor to observe more closely.

The video screen drop down list enables the user to select and instruct the server to play a selected video. The server selects these videos dynamically based on the current screen being displayed.

The warning bell button enables a member of the team to call for help in case of a problem. When a user presses this button, the client sends a message to the server that an alarm should be played on the other client computers. In this implementation, the alarm includes a visual alert screen and an audio alert generated on the other computers within the system. An alternative is to sound an audio alarm on the other computers. The alert is triggered through the addition of a record onto the message queue that all computers in the system are monitoring. The alert is cleared through the deletion of the record.

Finally, the notepad button launches a text editor in a window that enables the user to enter a medical note. The server records that date, time, the text entered by the user, and who made the observation.

Linking of Screens

As a user makes observations, the system evaluates whether the observations require supplemental information. Some observations can generate warnings in screens for other parts of the exam. To improve performance, the client maintains the patient's exam file in memory and issues context sensitive additional questions that are generated based on observations entered during the exam. As observations are made during the physical exam, the client executing the physical exam software determines when to present additional screens. The conditions that need to be satisfied to trigger additional exam screens are maintained in memory variables which control the operation and behavior of the exam as a whole, and the operation and behavior of individual sub-exam screens.

FIG. 6 illustrates an example of a supplemental screen that is triggered in response to an abnormal observation. In this example, the client prompts the user for more information with a supplemental screen because the user has entered an abnormal observation on the abdominal screen. The supplemental screen shown in FIG. 6 prompts the user to record any additional abnormalities from a predetermined list.

In addition to generating new questions and supplemental screens dynamically, another feature is the ability to launch other software processes in the system in response to an observation or a request to perform some treatment. For instance, if the doctor decides to prescribe a drug that is listed on a treatment list, the doctor can select that treatment by clicking on it. The client software will then launch a prescription screen so that the doctor can immediately fill the prescription. When the doctor completes the prescription and exits the prescription screen, the client sends a print job to the prescription printer. It then prints the label on the attached printer.

During the examination, the doctor may prescribe and dispense various treatments via additional user interface screens. One such screen, called the therapy screen, can be accessed via a drop down menu. As explained further below, this screen lists therapy service items that have been prescribed based on a previous diagnosis. When the doctor completes the service, he or she enters the change in status through the therapy screen. The server automatically adds service items completed during the visit to the client's invoice. The doctor can also use another screen, called the order screen, to prescribe and dispense a treatment item.

Graphical Displays Used to Enter Patient Observations

Figure 7:
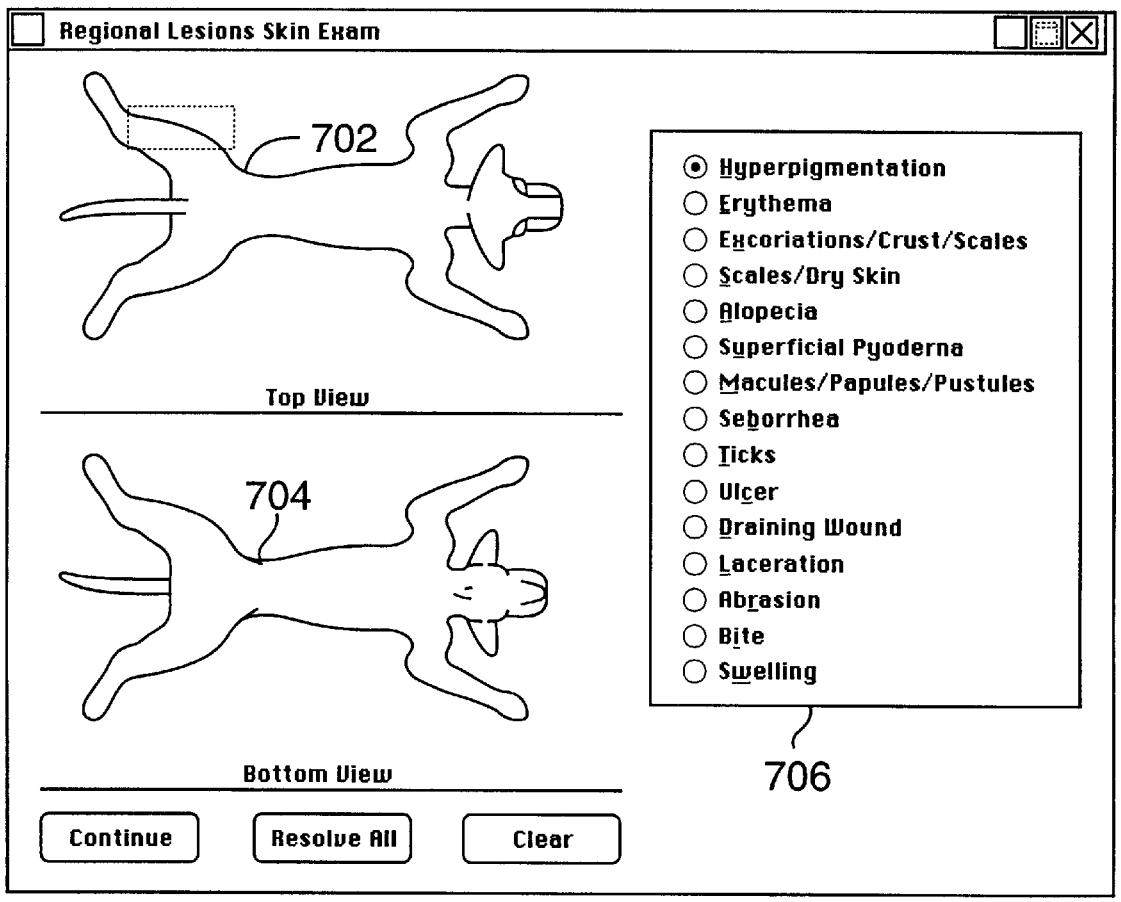
FIG. 7 is an example of an interactive user interface screen used to prompt the user for graphical input of medical observations using a graphical depiction of a patient's anatomy.

FIG. 7 is an example of a screen 700 used to prompt the user for graphical input of medical observations. In this example, the screen displays a graphical representation of the pet 702, 704 and enables the user to mark the location of lesions on the skin graphically. The graphical representation shows a part of the anatomy of the pet and is responsive to cursor input from a pointing devices such as a mouse, track ball, or touch screen. The user can mark the location of lesions on the patient using the cursor control device.

The type of observation (i.e. the type of lesion in this example) is entered via a selection list 706. First, the user selects the type of lesion by clicking on a selection in the list, and then marks the location of a lesion by positioning the cursor over the position on the graphical depiction of the skin where the lesion is located on the pet.

Each time the user clicks on the graphical representation, the client software records medical observations as observation records in a database file. These records include: the type of observation, top or bottom view, the date and time, the doctor-nurse team who recorded the observation, and the coordinates of the pixel where the user marked the lesion. These coordinates are mapped to actual bodily region (based on their location, e.g., pixel at (5, 19) is mapped to the dorsal paw).

Verification of the Exam

Figure 8:
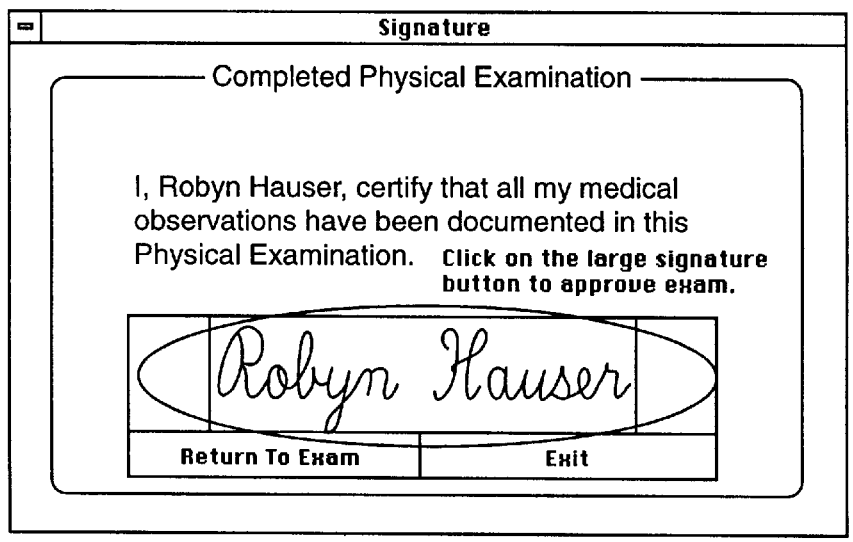
FIG. 8 is an example of a graphical display depicting the doctor's signature to prompt the doctor to verify medical observations entered into the system.

The physical exam software provides a user interface control that enables the doctor to record an event certifying that all of the observations have been documented. Specifically, the client software displays the dialog box shown in FIG. 8. The client software displays this dialog box in response to a user clicking on the exam complete button in the physical exam screen.

In order to complete an exam, the doctor must login to the system. After logging in, the doctor can review and edit the observations made by the nurse, perform treatment, etc. When complete, the doctor clicks on the exam complete button, which causes the client to display the signature box. The doctor's signature is stored as an image in the hospital database. The server ensures that the signature is inserted on all of the forms requiring a doctor's signature.

Diagnosis and Therapy Selection

When the physical exam is complete, the doctor can proceed to a diagnosis screen. FIG. 9 illustrates an example of the diagnosis screen. This screen is displayed in response to the doctor certifying that the exam is complete as explained above. The diagnosis screen includes the patient banner 902, a box for displaying abnormal observations 904, a box for displaying a rule out list 906, and a box for displaying tentative diagnosis 908. The box 910 labeled as "unresolved symptoms" keeps a running total of symptoms that are not linked to a diagnosis.

The diagnosis screen also includes a number of navigational controls used to navigate to other parts of the system or to launch other features. These controls include: 1) a "search for diagnosis" button 912 that launches the interface to a database search tool for keyword searching the system's list of diagnosis, 2) a "protocol" button 914 which launches a service for applying a protocol to the patient given the tentative diagnosis selected in the diagnosis screen, 3) a healthy pet button 916 which enables the team member to indicate that no diagnosis or treatment protocol need be selected, and 4) an exit button 918 used to exit the diagnosis screen and return to the main window of the client software.

When the exam is complete and certified, the client software on the exam PC sends a message to the server, which compiles a list of the abnormal observations in response and places them in a table. These abnormal observations are then displayed in the abnormal observation box 904. Each of the records in this list can be marked as either diagnosed or removed. To remove an observation, the doctor clicks on the "remove symptom" button 920. This button toggles between "remove symptom" and "use symptom in diagnosis" to enable the user to add a symptom back onto the list of abnormal observations.

The rule out list is a list of possible diagnosis automatically generated by the server. The rule out list is generated from a table that keeps a list of all ailments called the "all ailments table." Each item within the all ailments table has observations potentially associated with it. The actual observations made during the physical examination are matched against the list of observations associated with ailments. Ailments which match are then added to the diagnosis rule out list.

The doctor can select a diagnosis by clicking on an item in the rule out list. When the doctor does so, the client sends a message to the server indicating the selected diagnosis. The server removes the diagnosis from the rule out list, adds it to the tentative diagnosis, and determines which abnormal observations are linked to the diagnosis. It then marks the abnormal observations that are linked to the selected diagnosis with a "D." The server sends the results of these operations back to the client to update the display dynamically. In the display, the selected diagnosis moves to the tentative diagnosis box, the abnormal observations linked to the selected diagnosis are marked with a "D" and the unresolved symptoms count is updated to a number reflecting the number of abnormal observations that are undiagnosed and not marked as removed.

In the tentative diagnosis box, the client also displays the status of the diagnosis, as reflected in the diagnosis table maintained on the server. The possible status includes: Needs protocol, Undergoing Therapy, Client Postponed, and Client Declined. This status is updated automatically as the user takes actions that change the status of a diagnosis. For example in this version, the initial status of a selected diagnosis is "Needs Protocol." When the doctor places the cursor over a diagnosis in the tentative diagnosis box, it becomes highlighted. The doctor can then launch a protocol by clicking on the protocol button. In response, the client sends a message to the server, which changes the status of the diagnosis to Undergoing therapy. In addition, the server generates the protocol.

To generate a protocol, the server looks up the protocol in a protocol table using the selected diagnosis as a key. The protocol for a tentative diagnosis includes one or more (typically several) recommended therapy items, each having a status. When the user clicks on the protocol button, the server generates the protocol and sends the protocol items and status to the client. In turn, the client displays a diagnostic protocol screen.

FIG. 10 is an example of the diagnostic protocol screen used to manage a treatment protocol. The diagnostic protocol screen 1000 includes the patient banner 1002 (the same as in other screens described above), a tentative diagnosis box 1004, a recommended therapy box 1006, a diagnosis status check list 1008, and navigational control buttons 1010–1014 to link to other screens and launch other features.

The tentative diagnosis box 1004 lists the selected diagnosis from the diagnosis screen. The recommended therapy box 1006 lists the therapy items for the treatment protocol corresponding to the selected diagnosis. Note that the therapy items each have a status associated with them, either required or recommended. The doctor can change the status from recommended to required or vice-versa by clicking on a therapy item.

The diagnostic status check list 1008 includes a series of check buttons that enables the user to record the status of the treatment protocol for the selected diagnosis. This feature facilitates thorough record keeping and enables the medical practice to document that the protocol options were presented to the client and whether the client refused the treatment.

The navigational controls link to other screens and provide access to additional functions. One function is the estimate function, which causes the system to display a list of services, the status of the services, and a cost estimate. To access this function, the user clicks on the Estimate button. The estimate screen is described in further detail below.

The additional therapy button 1012 and continue button 1014 link to other screens. This enables the doctor to go to another screen to modify the therapy protocol.

The server compiles the services in the treatment protocol into a cost estimate. In addition, it forces follow-up in two important ways. First, it handles scheduling of the next visits and schedules follow-up calls. Second, it automatically adds prompting messages in future physical exam sessions to remind the provider team that certain observations are made and therapy service items are performed.

FIG. 11 is an example of the Estimate screen 1100. This screen can be accessed from several different screens in the physical exam and diagnostic software to show a cost estimate of product and service items that have been or are to be provided to the patient. Specifically, the cost estimated can be generated as service items are requested by the client during a visit or at the end of the visit. The Estimate screen is linked to the treatment protocol screen to give the client a cost estimate of all of the therapy service items that are to-be provided under the protocol.

The list of service items in the cost estimate is dynamically generated during patient visits, either as a result of the provider team selecting a product or service for the patient or the treatment protocol automatically adding therapy items to the list. In addition, if the patient is on a wellness plan, preventative care services are automatically added to this list when the plan is initiated. As items are prescribed for the patient, records are added to a table called the accounting sales line item table. Items added have an initial status code which indicates that the item is to be done. Once an item is completed, the status code is changed to reflect that the item is done. The status of each record reflects its status as an item which has been completed, or needs to be done. To generate a cost estimate, the server searches the accounting sales line item table in the status field to identify items that are completed and generates a list of completed items along with the cost of each item.

The Estimate screen 1100 includes the patient banner 1102, a service item box 1104, and several cost summary boxes 1106–1110. The screen also includes control buttons 1112, 1114 to print out a cost estimate and exit the screen. The services box 1104 lists the following records: a service item, its estimated cost, the name of the patient, and date completed.

The Estimate Screen estimates costs in three different categories: the wellness plan cost estimate 1106, the regular fee estimate 1108 and the client's estimate 1110.

The user can print an estimate by clicking on the print control button 1112. When the user exits the estimate screen, the client software returns to the physical exam screen. At this point, the doctor can proceed to provide the therapy for the patient. To generate the therapy screen for the patient, user selects Therapy: patient from a drop down menu.

FIG. 12 is an example of the therapy screen 1200 used to manage the administration of a therapy service item. The therapy screen displays all the items that have been prescribed to be administered to the patient. Additional information relating to dosage is also included. The therapy screen may optionally view the current medical record from a standpoint of all items prescribed, or only those items remaining to be performed. The therapy screen allows access to other screens such as the physical examination, the medical notes, diagnosis and ordering screens, via drop down menus, navigational controls, and user selection of therapy service items displayed on the screen. The therapy screen is accessible from other screens as well via a drop down menu and navigational control buttons.

The therapy screen 1200 includes a banner 1202, a box 1204 showing therapy service items and related attributes, a list of check buttons 1206 for selecting portions of the service table for viewing, a status control button 1208 for changing the status of selected service items; a print label button 1210 for printing labels, and a remove item button 1212 for removing selected therapy service items. This screen also includes a box 1214 for viewing the tentative diagnoses, including a list of diagnoses where each diagnoses has a date and status attribute. Finally, the therapy screen includes navigational buttons 1220–1226 used to link to other screens and access other functionality.

The box of therapy items 1204, in this version, includes a list of product and service items, with fields for the date the order was received, the quantity of the item, and the status. In the case of prescriptions, the box also displays dosage and frequency. This box 1204 enables the doctor to view a list of service items scheduled for a patient to keep track of what has been done and what needs to be done. When the doctor or other member of a provider team provides a product or service, the team member can update the status of a service item in the patient's data by selecting an item and indicating that it is done. For instance, the doctor can select items and press the "make all done" button to indicate that the status of these items has changed from "to-do" to "done." In response, the server dynamically updates the status of the data in the patient's database. The client sends a message to the server with the change in status so that the server data matches the status currently displayed on the screen of the client computer. In a similar fashion, the doctor can remove items from the list by selecting them and clicking on the "remove items" button 1212.

The print labels button is used to initiate a print process for printing a label for a prescription selected from the list of items in the list of therapy box 1204. When the user clicks on the print labels button 1210, the client sends a message to the server with the pertinent data about the prescription. The pharmacy computer then retrieves this message from the server and processes the request by initiating a print process to print a label with the information provided in the message.

The navigational buttons 1220–1226 link to other screens. For example, the physical exam button 1222 links to the physical exam screen.

Client Check Out

Figure 13:
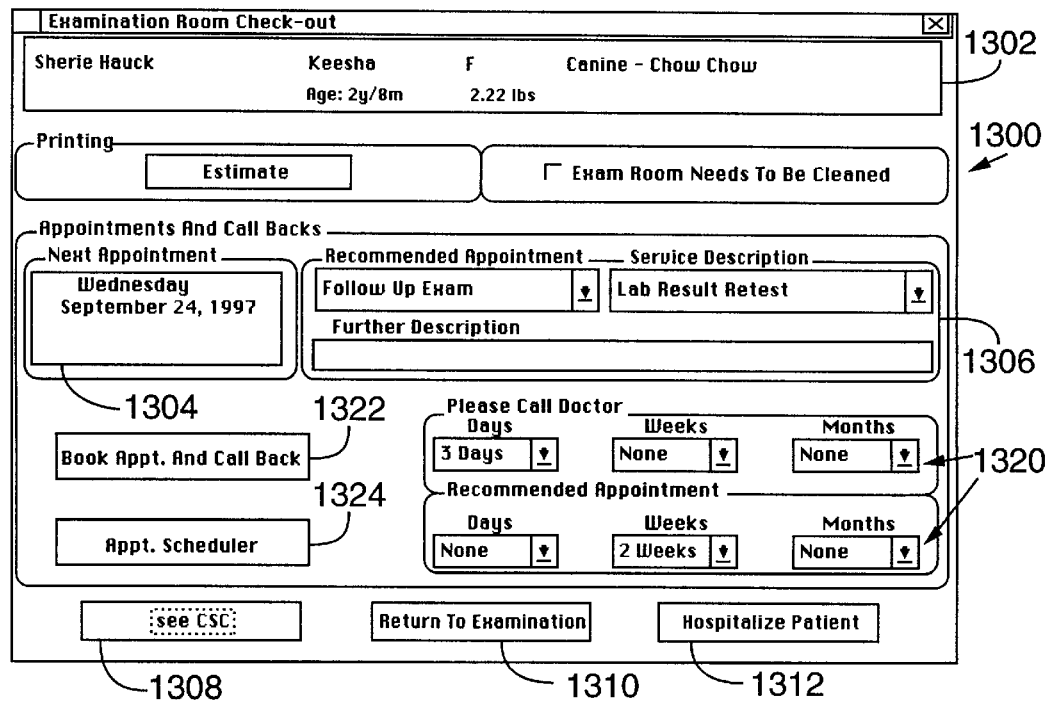
FIG. 13 is an example of an interactive user interface screen used to check a patient out of an exam room.

To complete a patient visit and transfer a patient's file to checking-out status, the doctor (or other member of the provider team) returns to the physical exam screen (FIG. 4) and then selects the Exam check-out button 402. This causes the client computer to display an exam room check out screen. An example of this window is shown in FIG. 13.

The exam room check out screen includes a patient banner 1302, a "next appointment" message box 1304, a service message box 1306, and control buttons 1308–1312, 1322–1324. The "next appointment" message box displays the next appointment scheduled for the patient from the patient's medical record stored on the server. The service message box 1306 is used to display and enter a service category, service description, and any additional descriptive information about a service item to be provided at an appointment. The user enters this information by selecting it from a predetermined list or entering it via the keyboard.

The exam room check out window includes a number of list boxes 1320 displaying "Days", "Weeks", and "Months" that enable the user to select an approximate time for a call-back or another appointment. When the user enters information in these boxes, the button 1322 shown as "Book Appt. And Callback" changes from "No Appt. Or Callback" to "Book Appt. And Callback" to reflect that an appointment is being scheduled.

After entering information for an appointment and/or callback, the user can click on the button labeled 1322 to cause the server to schedule the appointment or callback. The server has a scheduler program that can schedule appointments based on load (attempt to schedule appointments off-peak time periods). If the user requests an appointment by clicking on button 1322, a scheduler on the server will search for a time slot available near the approximate time entered by the user and enter a record of the appointment for the available time. For call backs, the scheduler will schedule a reminder for the provider team to call the client back at or before the approximate callback time entered by the user. If the user wants to view the available time slots and schedule an appointment directly, he or she can launch the user interface for the scheduler by clicking on the appointment scheduler button 1324. This brings the user to another screen used for the scheduler.

The "return to examination" button 1310 is a navigational control that allows the user to return to the main medical exam screen shown in FIG. 4. The "hospitalize patient" button is used to navigate to another screen to check the patient into the hospital and change the status of the patient to "hospitalized."

From the exam room check out screen 1300, the user can also issue an instruction to print an invoice of all the chargeable items provided during the visit. As products and services are provided during the visit, the provider team enters them. The server updates the status attributes in the patient's data base and also keeps a running list of the chargeable items in a separate invoice table. When a user instructs the client to print an invoice, the client computer sends a message to the server, which in turn, initiates a print process on the receptionist computer. The invoice is then printed at the printer in the receptionist area.

Once the user enters an appointment or notes that no appointment is necessary via the button 1322, the "See CSC" button 1308 becomes active (CSC means Customer Service Consultant). This button allows the user to navigate to the "Reception" screen shown in FIG. 14. When the user clicks on this button 1308, the status of the patient changes to "checking-out."

Figure 14:
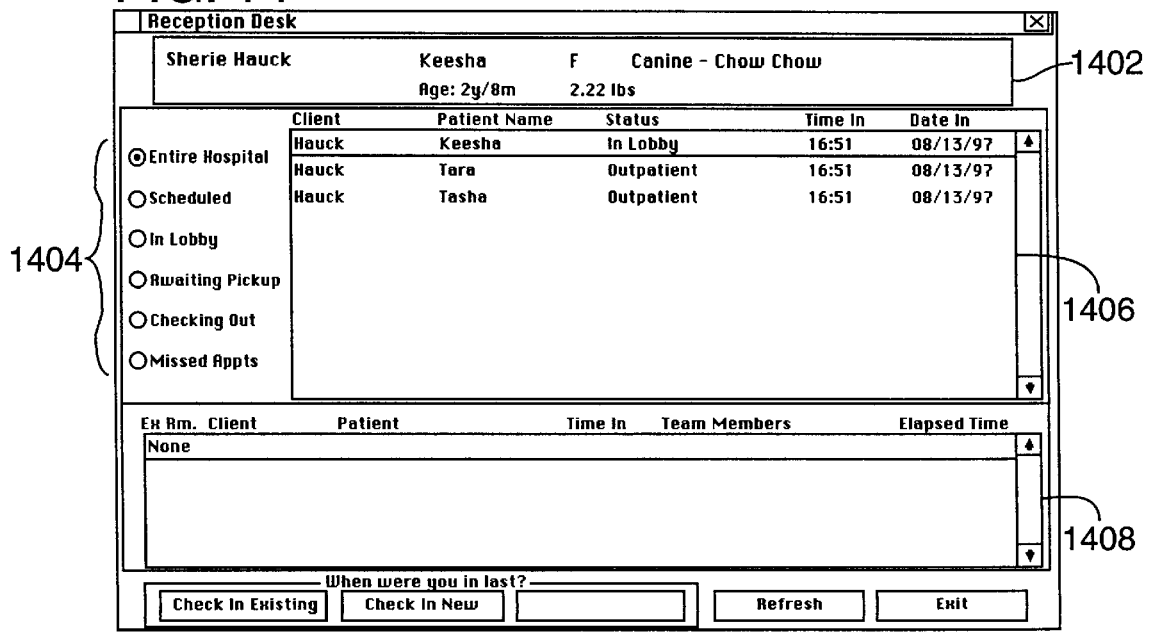
FIG. 14 is an example of an interactive user interface screen used to check patients in and out of a medical office and to monitor the status of patients in the office.

A user, typically the customer service consultant at the reception computer, checks a patient out of the facility at the reception desk screen 1400 shown in FIG. 14. This screen shows the patient's banner 1402, a list of check buttons 1404 for controlling the display, a box for viewing patient status 1406, and another box for viewing the status of the exam rooms 1408. The check buttons 1404 enable the user to control which patient status data is displayed in the box 1406. For example, if the user selects the button labeled "Entire hospital," box 1406 displays the status of patients in the entire hospital. If the user selects the button labeled "scheduled," the box 1406 only displays patients that are scheduled.

The reception screen also enables a user to check the status of patients in the medical exam rooms. The user can select (e.g., double-click on) a patient name from the lower box 1408 to display the status of the patient in an exam room, including a description of the service category (e.g., preventative care), the service description (e.g., vaccination), the time that the patient was checked into the exam room, and the elapsed time that the patient has spent in the exam room.

During the check out process, the receptionist returns any items left at the hospital, as reflected on a patient check in screen, which is accessible from a patient drop down menu at any time during operation of the system. The receptionist receives or confirms some form of payment and then checks the patient out of the hospital by selecting a check out option on the screen. When the receptionist checks the patient out, the patient's visit is over and the status of the patient is updated to reflect that the patient is checked out. At this point, the system discontinues tracking the time spent in the hospital.

Conclusion

While we have described the invention with reference to a specific implementation, we do not intend to limit the scope of the invention to this implementation. The system can be implemented in a client-server configuration, or in a single computer. In the latter case, both the client and server functions are performed on the same computer and the tables are maintained on this computer, rather than a remote server. The specific display format of the user interface screens can vary as well.

In view of the many possible embodiments to which the principles of our invention may be applied, it should be recognized that the illustrated embodiment is only a preferred example of the invention and should not be taken as a limitation on the scope of the invention. Rather, the scope of the invention is defined by the following claims. We therefore claim as our invention all that comes within the scope and spirit of these claims.

We claim:

1. A computer-implemented method for managing a medical exam, diagnosis, and treatment protocol of a patient, the method comprising:

displaying an interactive physical exam user interface on a display device;

in response to user selection during an interactive physical exam, displaying user interface screens that each guide the user through a part of the physical exam;

prompting a user to enter medical observations by displaying medical observations in the user interface screens and enabling the user to select from among the medical observations;

recording medical observations entered by the user in response to the user selecting from among the medical observations displayed in the user interface screens on the display device;

after receiving input indicating that the physical exam is complete, determining one or more possible diagnoses by matching the recorded observations with one or more ailments;

displaying possible diagnoses associated with the one or more ailments;

in response to the user selecting one of the displayed diagnoses, generating a treatment protocol for the diagnoses, and displaying the treatment protocol.

2. The method of claim 1 further including:

integrating the treatment protocol in subsequent patient visits by modifying user prompts presented to the user in a subsequent exam session to prompt the user to answer questions or enter medical observations related to the treatment protocol.

3. The method of claim 1 further including:

integrating the treatment protocol in subsequent patient visits by displaying status of scheduled therapy items in the interactive physical exam user interface along with a cost estimate of the scheduled therapy items.

4. The method of claim 1 further including:

scheduling therapy service items in the treatment protocol; and in subsequent exam sessions, determined by user login, displaying the scheduled therapy service items and associated status.

5. The method of claim 1 further including:

displaying a graphical representation of anatomy of the patient;

in response to cursor input on the graphical representation of the anatomy, recording location of an abnormal medical observation and type of the abnormal medical observation.

6. The method of claim 1 further including:

presenting an interactive user interface to record medical attributes of a patient;

searching a list of patient education videos to find a video that corresponds to one or more of the medical attributes of the patient; and playing the video corresponding to the medical attribute of the patient without explicit selection of a video by a user.

7. The method of claim 1 wherein the user interface screens guide the user through a complete physical exam before displaying a diagnoses by requiring the user to enter input acknowledging that the part of the physical exam associated with each user interface screen is complete.

8. A computer-implemented method for managing workflow in a medical facility, the method comprising:

displaying a plurality of different user interfaces on a display, where the user interfaces prompt a user for input about a patient and are associated with a stage in a visit of a patient to a medical facility;

guiding a user from one stage in the visit to a subsequent stage by requiring the user to enter patient data indicating that patient data has been observed before proceeding to a subsequent stage;

in response to user selection during an interactive physical exam, displaying user interface screens that each guide the user through a part of the physical exam;

recording the patient data in a medical record for the patient;

recording medical observations entered by the user in response to prompts for input displayed in the user interface screens on the display device;

after receiving input indicating that the physical exam is complete, determining one or more possible diagnoses by matching the recorded observations with one or more ailments;

displaying possible diagnoses associated with the one or more ailments;

updating patient status for the patient based on user input indicating that the patient has completed a stage in the visit; and displaying an indicator of current patient status.

9. The method of claim 8 wherein the stages include awaiting a medical exam, undergoing a medical exam, and checking out; and further including:
prompting a user for medical observations while the patient is undergoing the medical exam; and
requiring an authorized user to complete the medical exam before allowing a user to check the patient out of the medical exam.

10. The method of claim 9 wherein patient status is represented as awaiting medical exam when the patient is checked into the medical facility; and
wherein the patient status changes to undergoing a medical exam when the patient is checked into an exam room.

11. The method of claim 10 further including:
displaying a reception user interface screen to check a patient into a medical facility;
updating the status of the patient in response to receiving input sufficient to check the patient into the medical facility via the reception user interface.

12. A computer system for managing a medical practice in a medical facility comprising:
a computer network;
one or more reception computers in communication with the computer network, each programmed to check patients into and out of the medical facility; and
one or more exam room computers in communication with the computer network, each programmed to display an interactive user interface for guiding personnel through a medical examination, to record medical observations, to evaluate the recorded observations and to generate possible diagnoses dependent on the recorded observations, and to generate a treatment protocol for a selected diagnosis;
wherein the one or more exam room computers are programmed to display user interface screens that each guide the user through a part of a physical exam, to record medical observations entered by the user in response to prompts for input displayed in the user interface screens on the display device; to determine one or more possible diagnoses by matching the recorded observations with one or more ailments after receiving input indicating that the physical exam is complete, and to display possible diagnoses associated with the one or more ailments.

13. The computer system of claim 12 further including:
a treatment computer in communication with the computer network, wherein the treatment computer is programmed to record a treatment record for a patient when the treatment is provided to the patient.

14. The computer system of claim 12 further including:
a lab computer in communication with the computer network, wherein the lab computer is programmed to record lab results for a patient.

15. The computer system of claim 12 wherein the reception computer is programmed to update status of a patient when the patient is checked into an exam room to reflect that the patient has moved from one part of the facility to the next; and wherein the exam room computer is programmed to update status of the patient when the medical examination is complete to reflect that the patient has completed the medical examination.

16. The computer system of claim 15 including a server computer connected to the network, wherein the server computer is operable to store a list of patients checked into the medical facility, along with a status parameter indicating status of each patient in the medical facility; and
wherein the reception computer is programmed to query the server to obtain the status of each patient in the medical facility.

17. The computer system of claim 12 further including a server computer for storing a list of product or service items scheduled for patients, wherein each of the computers is programmed to access the server to update status of a specified product or service item in response to input indicating that the specified product or service item has been provided to a specified patient.

18. The computer system of claim 12 wherein the exam room computers are programmed to track identity of a provider who provides a product or service item to a patient by recording an indicator of a provider in response to input indicating that the product or service item has been provided to the patient.

19. The computer system of claim 12 further including:
a lab computer in communication with the computer network, wherein the lab computer is programmed to record lab results for a patient;
a treatment computer in communication with the computer network, wherein the treatment computer is programmed to record a treatment record for a patient when the treatment is provided to the patient; and
a server computer in communication with the computer network, wherein the server computer is programmed to respond to the reception, exam room, lab, and treatment computers to maintain and update medical records, including the lab results and treatment records for patients of the medical facility.

20. The computer system of claim 19 wherein the server computer is programmed to update status of patients in the medical facility in response to messages from other computers on the computer network indicating a change in patient status.

21. A computer readable medium having software for managing a medical exam, the software, when executed on a computer, performing the steps of:
displaying an interactive physical exam user interface on a display device;
in response to user selection during an interactive physical exam, displaying user interface screens that each guide the user through a part of the physical exam;
prompting a user to enter medical observations by displaying medical observations in the user interface screens and enabling the user to select from among the medical observations;
recording medical observations entered by the user in response to the user selecting from among the medical observations displayed in the user interface screens on the display device;
determining one or more possible diagnoses by matching the recorded observations with one or more ailments;
displaying possible diagnoses associated with the one or more ailments;
in response to the user selecting one of the displayed diagnoses, generating a treatment protocol for the diagnoses, and displaying the treatment protocol.

22. A computer-implemented method for managing a medical exam and diagnosis of a patient, the method comprising:
displaying an interactive physical exam user interface on a display device;

in response to user selection during an interactive physical exam, displaying user interface screens that each guide the user through a part of the physical exam;

prompting a user to enter medical observations by displaying medical observations in the user interface screens and enabling the user to select from among the medical observations;

recording medical observations entered by the user in response to the user selecting from among the medical observations displayed in the user interface screens on the display device;

after receiving input indicating that the physical exam is complete, determining one or more possible diagnoses by matching the recorded observations with one or more ailments; and displaying possible diagnoses associated with the one or more ailments.

* * * * *